United States Patent [19]
Curtis et al.

[11] Patent Number: 5,298,978
[45] Date of Patent: Mar. 29, 1994

[54] PIPETTE CALIBRATION SYSTEM

[75] Inventors: Richard H. Curtis, Gorham, Me.; Ann E. Rundell, West Lafayette, Ind.

[73] Assignee: Artel, Inc., South Windham, Me.

[21] Appl. No.: 843,446

[22] Filed: Feb. 28, 1992

[51] Int. Cl.$^5$ .................. G01B 11/28; G01N 21/00
[52] U.S. Cl. .................................. 356/379; 356/243; 356/435; 356/320; 356/326; 250/577
[58] Field of Search ............... 356/379, 243, 432–436, 356/439, 440, 381, 382, 319, 320, 325, 326; 250/573, 577, 576

[56] References Cited

U.S. PATENT DOCUMENTS

| | | | |
|---|---|---|---|
| 3,737,237 | 6/1973 | Zurasky | 356/382 |
| 3,869,211 | 3/1975 | Watanabe et al. | 356/381 |
| 4,128,339 | 12/1978 | Yamazaki et al. | 356/434 |
| 4,354,376 | 10/1982 | Greenfield et al. | 356/243 |
| 4,805,623 | 2/1989 | Jöbsis | 356/41 |
| 5,092,677 | 3/1992 | Curtis | 356/418 |
| 5,125,747 | 6/1992 | Sayegh et al. | 356/243 |

FOREIGN PATENT DOCUMENTS

0431578A2  6/1991  European Pat. Off. .

OTHER PUBLICATIONS

Cohn et al., "Precision Techniques For Measuring Liquid Quantity," Control Engineering, vol. 15, Jan. 1968, U.S., pp. 51–55.

Primary Examiner—Richard A. Rosenberger
Assistant Examiner—Hoa Q. Pham
Attorney, Agent, or Firm—Wolf, Greenfield & Sacks, P.C.

[57] ABSTRACT

Methods and apparatus for accurately determining the volume of a pipette using a photometer. A reagent system for use with the photometer includes a first container holding a reference solution and at least one second container holding a sample solution. A container holding the reference solution having maximum absorbance at a first wavelength is positioned in the photometer. The absorbances of the container at the first wavelength and at a second wavelength are measured. Then the optical pathlength of the container at the second wavelength is calculated from the measured absorbances at the first and second wavelengths. An aliquot of the sample solution is introduced into the container with a pipette to be calibrated. The sample solution has maximum absorbance at the second wavelength. The sample solution is mixed with the reference solution to form a mixture. Then the absorbance of the mixture in the container is measured at the second wavelength. The volume of the aliquot is calculated from the absorbance of the mixture and the optical pathlength of the container. The volume of the aliquot represents the volume of the pipette.

30 Claims, 6 Drawing Sheets

PIPETTE CALIBRATION SYSTEM

FIELD OF THE INVENTION

This invention relates to a system for accurately determining the volume of a vessel such as a laboratory pipette and, more particularly, to methods and apparatus for determining the volume of a pipette using a photometer.

BACKGROUND OF THE INVENTION

A pipette is typically used in laboratories for measuring and transferring small volumes of liquids. When the pipette volume must be known accurately, it is necessary to calibrate the volume of the pipette. A number of prior art techniques are known for volume calibration of pipettes.

In a prior art gravimetric technique, water is dispensed from a pipette being calibrated onto a sensitive balance. The water is weighed and the volume is calculated based on the weight of the water. Although this technique can provide accurate measurement of pipette volume, it is relatively expensive and complex when performed properly. For small volume pipettes, the required balance is relatively expensive. Furthermore, the accuracy is sensitive to evaporation of the water, the temperature of the water, the ambient barometric pressure, static electricity, vibration and ambient air movement.

In a prior art colormetric technique for calibration of pipette volume, a cuvette is provided with a predetermined volume of water or other solvent. A liquid containing a single dye is transferred from a pipette being calibrated into the cuvette and mixed. The cuvette is then positioned in the spectrophotometer and the absorbance of the liquid is measured. The volume of the pipette is calculated from the absorbance of the liquid in the cuvette. This technique is subject to inaccuracies, including optical variations and temperature variations. Typically, one aliquot of dye solution is added to the water in the cuvette and a measurement is taken. Then, the liquid in the cuvette is discarded and the same process is repeated several times to insure repeatability. This process is relatively inaccurate and time consuming. In particular, the variation in pathlength between each cuvette leads to inaccuracies, as well as the variation in pathlength when an individual cuvette is repositioned in the photometer between readings.

In a third prior art technique, the pipette being calibrated is used to transfer an acid solution into a container. Then a mechanical burette is used to add a base solution containing an indicator dye to the container. The indicator dye changes color when the concentration of acid equals the concentration of base. At this point, the volume of base added is read from the mechanical burette. This technique is relatively difficult and time consuming.

It is a general object of the present invention to provide improved methods and apparatus for calibrating the volume of a pipette or other vessel.

It is another object of the present invention to provide a reagent system for determining the volume of a pipette utilizing a photometer.

It is a further object of the present invention to provide methods and apparatus for determining the volume of a pipette with high accuracy.

It is still another object of the present invention to provide methods and apparatus for determining the volume of a pipette with a photometer which do not require a highly accurate container for measurement.

It is yet another object of the present invention to provide methods and apparatus for determining the volume of a pipette which are easy to use and low in cost.

SUMMARY OF THE INVENTION

According to the present invention, these and other objects and advantages are achieved in a method for determining the volume of a vessel such as a pipette using a photometer. The method comprises the steps of positioning a container in a photometer, the container holding a known amount of reference solution having maximum absorbance at a first wavelength, measuring the absorbance of the container at the first wavelength and at a second wavelength, calculating the optical pathlength of the container at the second wavelength from the measured absorbances at the first and second wavelengths, introducing an aliquot of a sample solution into the container from a vessel to be calibrated, the sample solution having maximum absorbance at the second wavelength and mixing the sample solution with the reference solution to form a mixture, measuring the absorbance of the mixture in the container at the second wavelength, and calculating the volume of the aliquot from the absorbance of the mixture and the optical pathlength of the container, based on the known volume and concentration of the reference solution and the known concentration of the sample solution, and wherein the volume of the aliquot represents the volume of the vessel.

The vessel typically comprises a pipette. The reference solution preferably comprises copper sulfate dissolved in a pH 7.0 buffer and has maximum absorbance at about 730 nanometers (nm). The sample solution preferably comprises Acid Red 1 dissolved in a pH 7.0 buffer and has maximum absorbance at about 520 nm.

In a preferred embodiment, the steps of introducing an aliquot of sample solution into the container, measuring the absorbance of the mixture and calculating the volume are repeated to provide multiple measurements of the vessel volume without emptying the container or moving the container from its position in the photometer.

The step of calculating the optical pathlength preferably includes correcting the optical pathlength for zero offset representative of a difference between the absorbance of the container at the first wavelength and the absorbance of the container at the second wavelength. The step of calculating the optical pathlength preferably further includes correcting the optical pathlength for a difference between the pathlength of the container at the first wavelength and the pathlength of the container at the second wavelength. The step of calculating the volume preferably includes calculating the volume using Beer's law and correcting the calculated volume for deviations from Beer's law.

Typically, the ambient temperature is measured before the volume of the vessel is determined. The step of calculating the volume preferably includes correcting the measured absorbance of the mixture for a difference between the absorbance at the measured ambient temperature and the absorbance at a reference temperature. The step of calculating the volume preferably further includes correcting the calculated volume for a difference between the volume at the measured ambient temperature and the volume at the reference temperature.

According to another aspect of the invention, there is provided a system for use with a photometer in determining the volume of a vessel such as a pipette. The system comprises a first container holding a predetermined volume of a reference solution containing a predetermined concentration of a first material having maximum absorbance at a first wavelength for positioning in the photometer for determination of the optical pathlength of the container, and a second container holding a sample solution containing a predetermined concentration of a second material having maximum absorbance at a second wavelength for transfer with the vessel of an aliquot of sample solution from the second container to the first container for measurement of the absorbance of the mixture of reference and sample solutions at the second wavelength and for determination of the volume of the aliquot from the optical pathlength of the first container and the absorbance of the mixture, based on the known volume and concentration of the reference solution and the known concentration of the sample solution, and wherein the volume of the aliquot represents the volume of the vessel.

According to another aspect of the invention, there is provided a system for determining the volume of a vessel such as a pipette. The system comprises a photometer, a container holding a predetermined volume of a reference solution having maximum absorbance at a first wavelength positioned in the photometer, the photometer including means for measuring the absorbance of the container holding the reference solution at the first wavelength and at a second wavelength, means for calculating the optical pathlength of the container at the second wavelength from the measured absorbances at the first and second wavelengths, the photometer including means for mixing the reference solution with an aliquot of sample solution transferred to the container with a vessel to be calibrated to form a mixture and means for measuring the absorbance of the mixture at the second wavelength, and means for calculating the volume of the aliquot from the measured absorbance of the mixture and the optical pathlength of the container, based on the known volume and concentration of the reference solution and the known concentration of the sample solution, and wherein the volume of the aliquot represents the volume of the vessel.

According to still another aspect of the invention, there is a provided a method for measuring the optical pathlength of a container to be used for absorbance measurements at a predetermined wavelength. The method comprises the steps of positioning a container in a photometer, the container holding a reference solution having maximum absorbance at a first wavelength that is different from the predetermined wavelength, measuring the absorbance of the container at the first wavelength and at the predetermined wavelength, and calculating the optical pathlength of the container at the predetermined wavelength from the measured absorbances at the first wavelength and the predetermined wavelength.

BRIEF DESCRIPTION OF THE DRAWINGS

For a better understanding of the present invention, together with other and further objects, advantages and capabilities thereof, reference is made to the accompanying drawings which are incorporated herein by reference and in which.

DETAILED DESCRIPTION OF THE INVENTION

The present invention provides methods and apparatus for accurately determining, or calibrating, the volume of a vessel such as a laboratory pipette using a photometer. The technique is typically used for calibrating the volume of pipettes in the size range from 5 microliters to 500 microliters. However, the invention can be utilized for calibrating vessels having volumes outside this range. The major components required to determine the volume of a pipette are a photometer and a calibration reagent system. A printer is preferably used to record the results.

Figure 1:
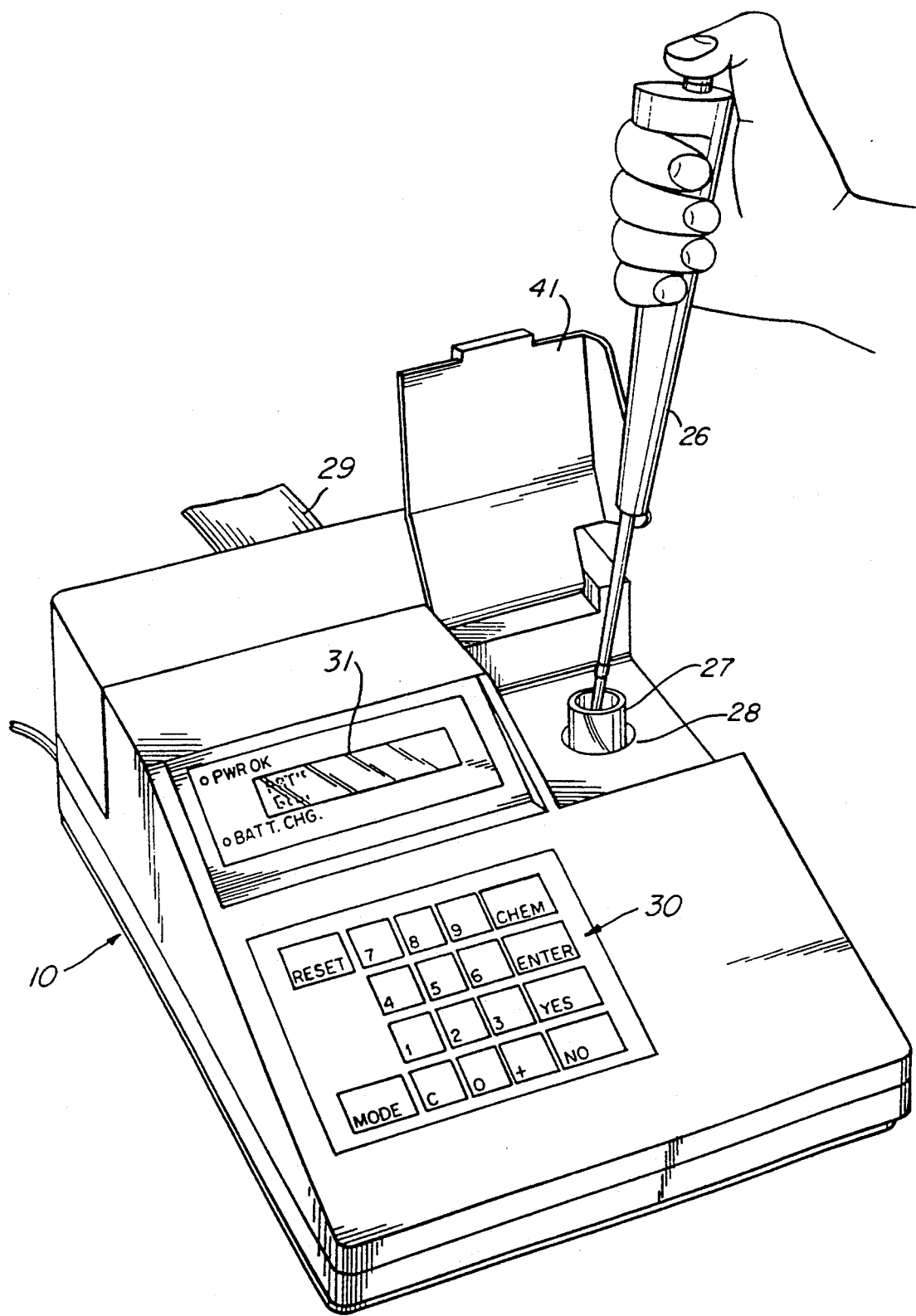
FIG. 1 is a perspective view of a photometer suitable for use in the pipette volume calibration technique of the present invention.
Figure 3:
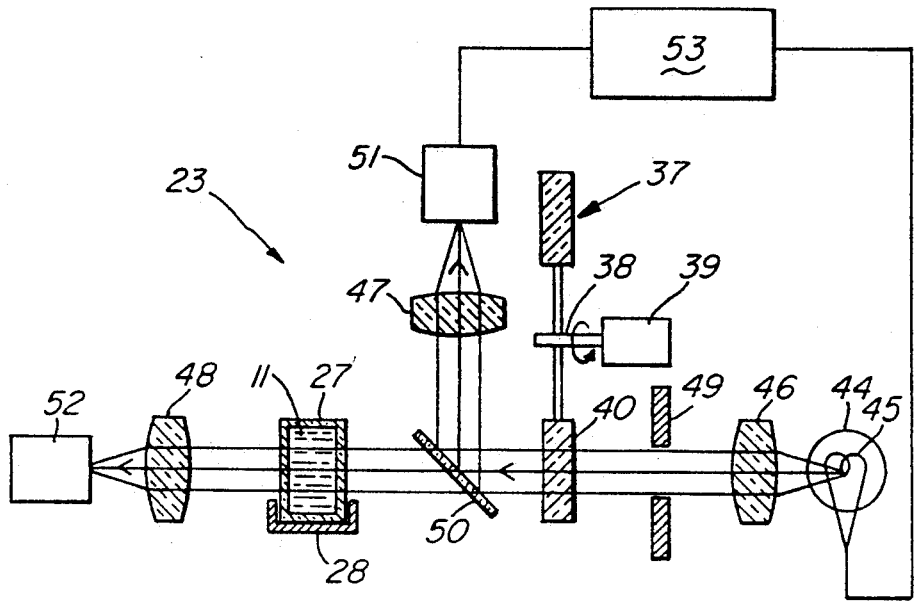
FIG. 3 is a schematic diagram illustrating the optics of the photometer utilized for absorbance measurements.
Figure 4:
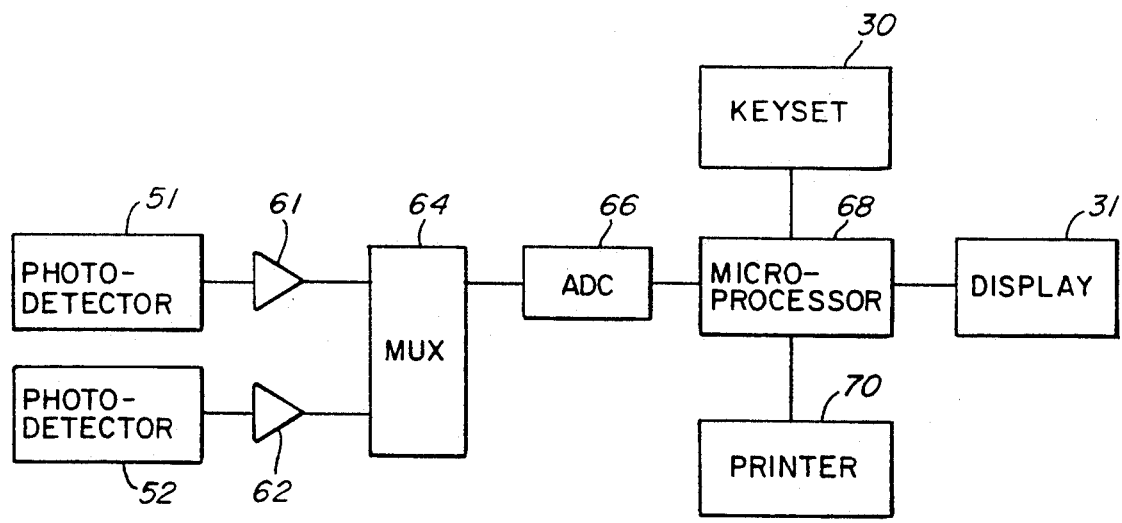
FIG. 4 is a block diagram of the major electronic components of the photometer.

A preferred photometer is shown in FIGS. 1, 3 and 4, and described more fully in U.S. Pat. No. 5,092,677, entitled "Photometer Having A Long Lamp Life, Reduced Warm-Up Period And Resonant Frequency Mixing," issued Mar. 3, 1992, and which is hereby incorporated by reference in its entirety. The photometer instrument 10 shown in FIG. 1 is a wavelength selectable photometer with the ability to handle the mixing and photometric measurement requirements of a pipette volume calibration. The instrument is operated via a keypad 30 and communicates information to the operator via an alphanumeric display 31, a printer 70 (FIG. 4) connected to a cable 29, and through audible and visual signals at specific points during and at the conclusion of each calibration. A hinged lid 41 covers a cuvette 27 (FIG. 3) containing a solution to be analyzed. The cuvette 27 is held in holder 28 in a compartment under lid 41, which allows samples to be added directly to the cuvette from a pipette 26 while in the photometer.

A schematic diagram of the optical assembly 23 of the photometer is shown in FIG. 3. Light generated by a lamp 44 is collimated to parallel rays by a lens 46, and an aperture 49 restricts the rays to a collimated beam of small diameter. The lamp is a tungsten filament bulb filled with an inert gas such as krypton or argon; this lamp has a reduced warm-up period and the inert gas minimizes evaporation of tungsten atoms from the filament 45, thus allowing higher operating temperatures. The beam passes through a filter 40 which selects a wavelength suitable for the test being run. The filter 40 is one of a plurality of filters mounted in a filter wheel 37 which is rotated via a shaft 38 by a filter wheel motor 39. The light beam is then split into two parts by a partially reflective beam splitter 50 which reflects about 10% of the beam to a reference photodetector 51 via a lens 47. Ninety percent of the beam passes through beam splitter 50 and through a solution 11 in cuvette 27 in cuvette holder 28. A portion of the light beam is absorbed by the solution and the remainder is transmitted through a lens 48 to a photodetector 52. The intensity of lamp 44 is regulated by feedback control circuit 53 which receives an input from reference photodetector 51 and causes the source intensity to asymptotically approach a final and stable value in a smooth and substantially exponential curve. The absorbance of the solution 11 in cuvette 27 is determined by comparing the outputs of photodetectors 51 and 52. The outputs of the reference and sample photodetectors are taken at different times while the source intensity approaches a final stable value to compensate for variations in the light source intensity over the time period during which the outputs are taken.

A block diagram of the electronics portion of the photometer is shown in FIG. 4. The outputs of photodetectors 51 and 52 are directed through preamplifiers 61 and 62, respectively, and a multiplexer 64 to an analog-to-digital converter 66. The analog-to-digital converter 66 digitizes a selected photodetector output and provides an input to a microprocessor 68. The microprocessor 68 receives the absorbance measurements from photodetectors 51 and 52 and calculates pipette volume as described in detail below. In addition, the microprocessor 68 calculates statistics and provides outputs to printer 70.

Figure 2:
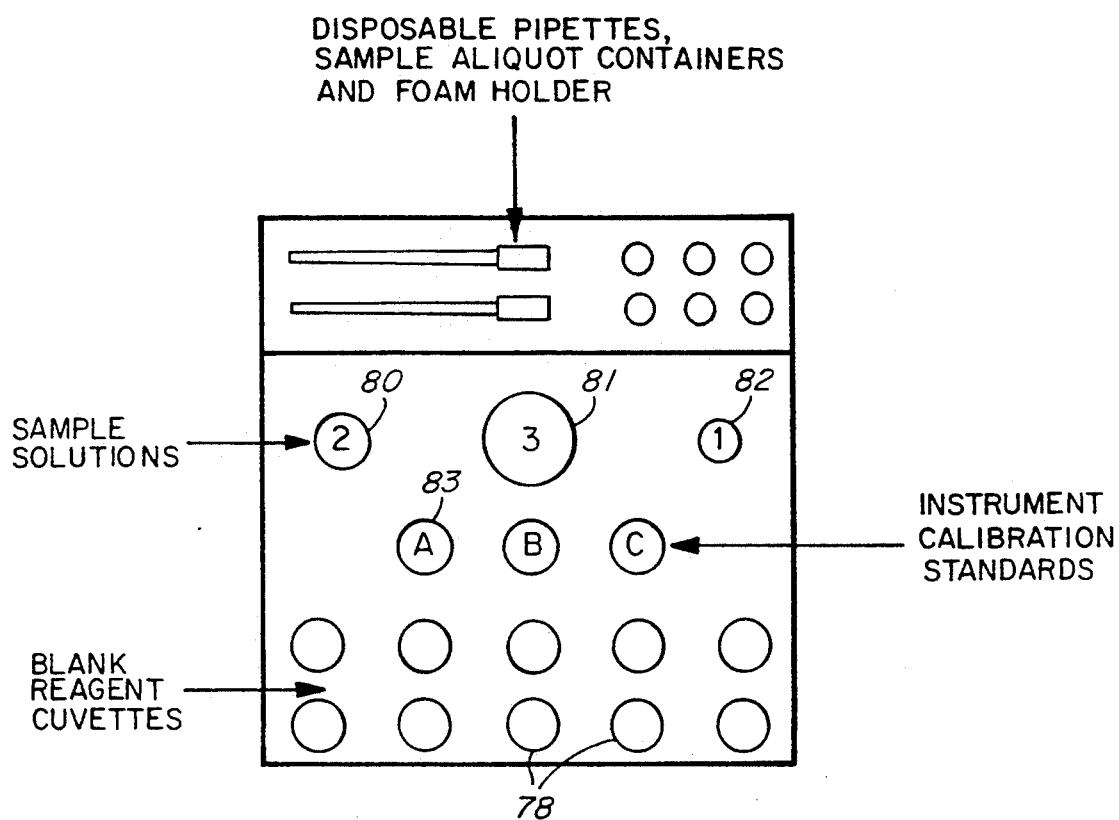
FIG. 2 is a schematic representation of a reagent system used with the photometer for pipette volume calibration in accordance with the present invention.

A suitable reagent system for performing pipette calibration is illustrated schematically in FIG. 2. A number of blank reagent cuvettes 78, which correspond to cuvette 27 in FIG. 3, each hold a predetermined volume of a reference solution as described below. Containers 80, 81 and 82 hold predetermined concentrations of sample solutions. Sample solutions with different concentrations are used for measuring pipettes in different size ranges. In a preferred embodiment, container 82 holds a sample solution for pipettes in the range of 5 microliters to 20 microliters, container 80 holds a sample solution for calibration of pipettes in the range of 21 microliters to 100 microliters, and container 81 holds a sample solution for calibration of pipettes in the size range of 101 microliters to 500 microliters. The reagent system further includes containers holding instrument calibration solutions A, B and C, disposable pipettes and sample aliquot containers.

The reagent system and the measurement technique are based on the application of Beer's law which is expressed as follows.

$$A = Cl\epsilon \qquad (1)$$

where A is the absorbance of the solution, C is the concentration of an absorbing species, l is the pathlength of the light through the solution and $\epsilon$ is the molar absorptivity of that species. As discussed below, the absorbance measurements made by the the photometer are used to determine volume.

The calibration system uses two types of reagents, a reference solution and a sample solution. The reference solution consists of copper sulfate dissolved in pH 7.0 buffer with EDTA in solution. The blank reagent cuvettes 78 shown in FIG. 2 are prefilled with exactly 3.5 milliliters of reference solution and are tightly capped. The sample solution is Acid Red 1 dissolved in pH 7.0 buffer. As indicated above, there are three concentrations of sample solutions to permit a range of pipette volumes to be calibrated.

Figure 5:
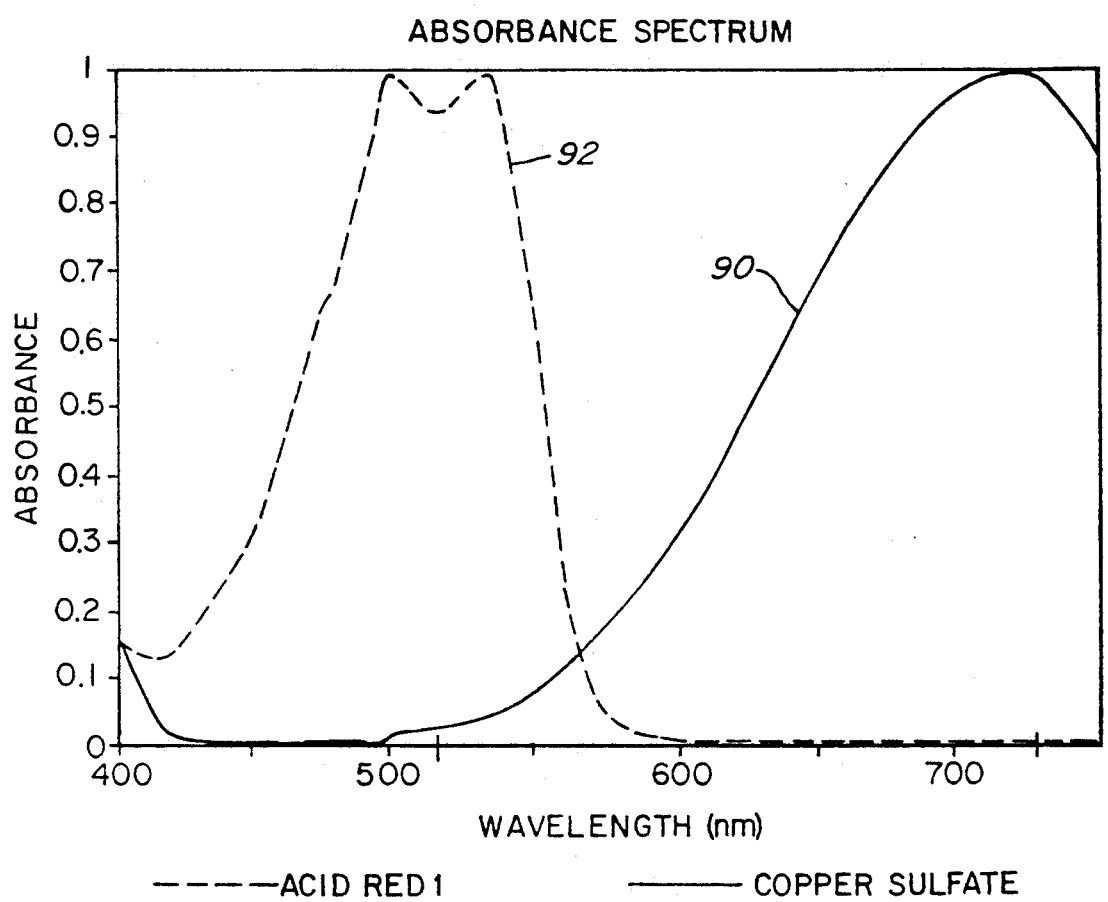
FIG. 5 is a graph of absorbance as a function of wavelength showing the absorbance spectra for copper sulfate and Acid Red 1.

The reference and sample solutions constitute dyes which work together to permit accurate pipette volume calibration. As shown in FIG. 5, the dyes have different absorbance peaks. As indicated by curve 90 in FIG. 5, copper sulfate (dye B) has an absorbance peak at about 730 nm. As indicated by curve 92, Acid Red 1 (dye A) has an absorbance peak at about 520 nm. Furthermore, there is little overlap between the absorbance spectra. At 520 nm, the absorbance of copper sulfate is relatively small and at 730 rim, the absorbance of Acid Red 1 is relatively small.

The technique for determining pipette volume in accordance with the present invention is based in general on first determining the optical pathlength of the cuvette that is placed in the photometer for holding the solutions to be measured. It will be understood that variations in thickness and absorbance of the cuvette walls affect the optical pathlength. In practice, it has been found that cuvettes of acceptable cost vary by about 2% in optical pathlength. Furthermore, the cuvettes may not be perfectly round and thus vary in optical pathlength depending on their orientation in the photometer. Since it is desired to determine pipette volume with an accuracy of 1% or less, it is necessary to determine the optical pathlength of each cuvette when positioned in a predetermined orientation in the photometer.

After the optical pathlength of the cuvette has been determined, the volume of the pipette being calibrated is determined. In general, the volume measurement technique is based on dilution of the reference solution in the cuvette with a sample solution transferred into the cuvette by the pipette being calibrated. The aliquot of sample solution transferred into the cuvette corresponds to the volume of the pipette. The reference solution and the sample solution are mixed, and the absorbance of the mixture is measured at the wavelength where the sample solution has maximum absorbance. The increase in absorbance of the mixture depends on the volume of the sample solution added from the pipette being calibrated. The technique for pipette volume calibration is described in detail below.

Figure 6:
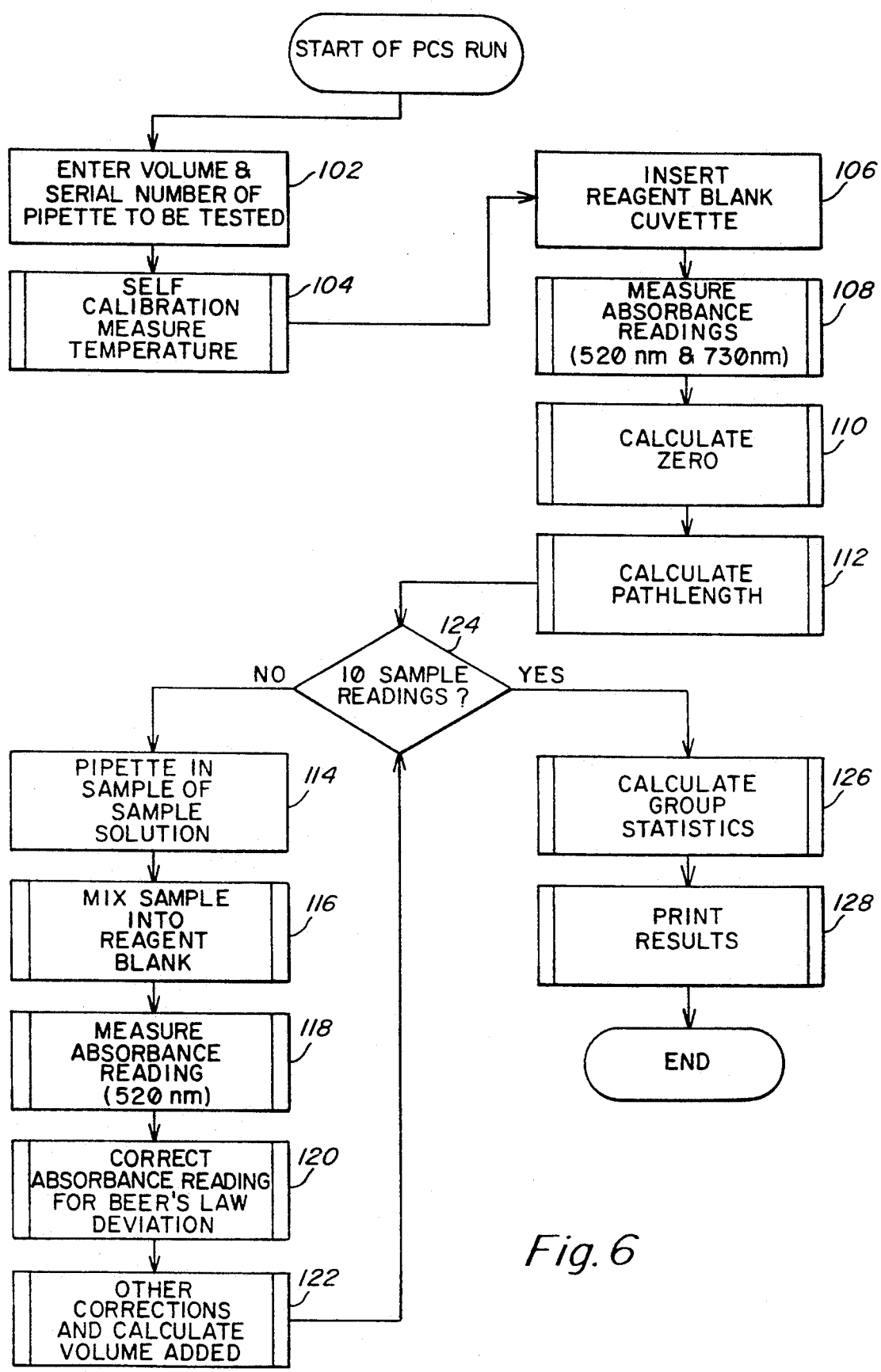
FIG. 6 is a flow diagram of the method for pipette volume calibration in accordance with the present invention.

A flow diagram of the volume calibration procedure in accordance with the present invention is shown in FIG. 6. Initially, the nominal volume and serial number of the pipette to be calibrated is entered through keypad 30 in step 102. This information is used subsequently in printing the results of the calibration. Then the photometer performs a self-calibration in step 104, during which the ambient temperature is measured and stored for later use. The photometer includes a thermistor for measurement of ambient temperature. Then, the user inserts a blank reagent cuvette 78 into the photometer through hinged lid 41 in step 106. The blank reagent cuvette 78 is located in the photometer in the position of cuvette 27 shown in FIG. 3 so that the light beam passes through the cuvette and the solution contained in it. As indicated above, the blank reagent cuvette 78 contains a predetermined volume of copper sulfate dissolved in a pH 7.0 buffer. The copper sulfate has a known concentration, typically 0.003350 molar. The photometer makes absorbance measurements of the blank reagent cuvette at 730 nm and 520 rim in step 108. Then, the zero is calculated in step 110 and the pathlength of the blank reagent cuvette 78 is calculated in step 112.

In a preferred embodiment, the blank reagent cuvettes 78 are borosilicate glass vials having a nominal diameter of 21 millimeters. The nominal pathlength is 18.4 millimeters. The terms "cuvette" and "vial" are used interchangeably herein to refer to the container that is placed in the photometer for absorbance measurements. As indicated above, there is a 2% tolerance on the pathlength and the vials are not perfectly round, so that the measured pathlength depends on the orientation of the vial in the photometer.

The relatively poor accuracy of the pathlength specification would degrade the overall accuracy of the volume calibration if it were not corrected. The technique selected to deal with this inaccuracy is to measure the pathlength of each vial as it is positioned in the photometer ready for use. Thus, variations in pathlength, due either to orientation of the vial in the photometer or due to diameter variations, are taken into account as the results are calculated.

The optical pathlength for each vial is determined individually in the following way. As indicated above, a copper sulfate dye solution having an absorbance peak at 730 rim is used as a reference solution in the blank reagent cuvette 78. The absorption of copper sulfate at a wavelength of 520 nm is quite small. After the cuvette is loaded into the photometer, absorbance measurements are made at these two wavelengths (step 108). The difference in absorbance measurements at the two wavelengths is related to the difference in absorptivities according to Beer's law as given in Equation (1) above. These values are used to solve for the pathlength l as follows.

$$l = \frac{A_{730} - A_{520}}{C_B (\epsilon_{B2} - \epsilon_{B1})} \quad (2)$$

where l is the optical pathlength, $A_{730}$ is the measured absorbance at 730 nm, $A_{520}$ is the measured absorbance at 520 nm, $C_B$ is the known concentration of dye B (copper sulfate) and $\epsilon_{B2}$ and $\epsilon_{B1}$ are the absorptivities at wavelengths of 730 nm and 520 nm, respectively.

Two minor corrections are made to the calculated optical pathlength in order to make the determination more accurate. A first correction is made for zero offset. The vial itself absorbs slightly differently at the two wavelengths so that a vial filled with clear pH 7.0 buffer shows a difference in absorbance between 520 nm and 730 Typically, the difference in absorbance is approximately 0.01. There is a also a slight instrument variation in this measurement.

The zero offset is measured each time the photometer is turned on. The display 31 prompts user to insert the CAL A calibration vial 83 (FIG. 2), which contains a clear pH 7.0 buffer without dyes. The difference in absorbance (zero offset), $A_{off}$, is measured and stored for use later in the day. The zero offset is used to correct the absorbances measured for the blank reagent cuvette at run time, providing a corrected pathlength of $$l' = \frac{A_{730} - A_{520} - A_{OFF}}{C_B (\epsilon_{730} \epsilon_{520})}$$

It is assumed that the blank reagent cuvette 78 has the same zero offset (within 0.001) as the CAL A calibration vial 83.

A second correction accounts for the fact that the effective optical pathlength of the vial is not independent of measurement wavelength. The reason for this dependence is that the vial is round, and the light beam entering the vial is fairly broad (about 4 millimeters in diameter) and is refracted at the glass-air interface, both on entering and leaving the vial. The amount of refraction is dependent on the index of refraction of the glass at the measurement wavelength. The dependence of optical pathlength on wavelength is measured as described below to provide a correction factor $F_{\lambda corr}$ to be used in the pathlength calculation. After the correction factor $F_{\lambda corr}$ is determined, it is applied to all calibration calculations. It is not necessary to remeasure the correction factor for each vial, since the value is consistent between vials and depends only on the dispersion of the glass type used in making the vial. The optical pathlength at 520 nm is thus given by $$l_{520} = \frac{F_{\lambda corr}(A_{730} - A_{520} - A_{OFF})}{C(\epsilon_{B2} - \epsilon_{B1})} \quad (4)$$

The correction factor $F_{\lambda corr}$ was determined as follows. A highly precise square glass cuvette with optical pathlength known to 0.1% as measured mechanically was used. A solution of dye B copper sulfate with absorbance peak at 730 rim was introduced into the square cuvette and into a standard round vial. The absorbances were measured for the square cuvette and round vial at 730 nm. Then, the experiment was repeated with dye A Acid Red 1 at 520 nm. It was assumed that since the square cuvette has plane sides perpendicular to a well collimated light beam, there is no reason for a difference in pathlength between 730 nm and 520 rim in the square cuvette. The desired correction factor is thus given by $$F_{\lambda corr} = \frac{l_{520}}{l_{730}} = \frac{A \text{ round }(520)}{A \text{ square }(520)} \cdot \frac{A \text{ round }(730)}{A \text{ square }(730)} \quad (5)$$

where A round (520), A square (520), A square (730) and A round (730) represent absorbance measurements of square cuvette and round vial at the indicated wavelengths. The results from a total of five such measurements are $F_{\lambda corr} = 1.0082 \pm 0.0002$. Care was taken to avoid moving the square cuvette or the round vial during the experiments since it would significantly reduce the accuracy of the results. All solutions were pipetted in and out, with the vial and cuvette remaining stationary in the photometer.

The contents of the blank reagent cuvette 78 are mixed prior to measurement of absorbance in step 108, thereby stirring up any particles which may be present so that they are included in the zero measurement at 520 nanometers. Although the bottling procedure takes great care to avoid particulates in the vials, some particles are inevitably present. It is important that the zero measurement be taken under exactly the same conditions as the subsequent measurements. The results of the absorbance measurement is A(O) and is expressed relative to the CAL A reading which was taken earlier in the day when the instrument was turned on. The value is not zero for three reasons:

a) The CAL A vial and the vial used for absorbance measurements during a volume calibration contain irregularities in the glass walls. The zero readings for two different vials or even the same vial after rotation can differ by 0.01. The difference is called $A_0$.

b) The zero on the photometer may have drifted over the intervening period of time since the CAL A vial was read. The instrument drift is included in $A_0$.

c) The blank solution of copper sulfate has a small absorbance at 520 rim given by $\epsilon_{B1}C_B l$ relative to the absorbance of the clear pH 7.0 buffer in the CAL A vial.

Thus, $A_0$ is given by $$A_0 = A(o) - \epsilon_{B1}C_B l \qquad (6)$$

After the vial pathlength has been determined as described above, measurements of pipette volume are taken. Referring again to FIG. 6, a pipette being calibrated having a volume $P_1$ is used to pipette an aliquot of sample solution containing dye A Acid Red 1 with concentration $C_A$ and absorptivity $\epsilon_{A1}$ at 520 nm to the blank reagent cuvette 78 in the photometer in step 114. The sample solution and the reference solution in the vial are mixed by the photometer in step 116 to form a mixture. The orientation of the vial in the photometer is not changed during this process so there is no reason for $A_0$ to change. The vial initially contained a volume $V_B$ of reference solution having dye B copper sulfate at concentration $C_B$ and absorptivity $\epsilon_{B1}$ at 520 nm. The absorbance $A(1)$ of the vial containing the mixture at 520 rim is given by $$A(1) = A_0 + \frac{P_1 C_A \epsilon_{A1} l}{P_1 + V_B} + \frac{V_B C_B \epsilon_{B1} l}{P_1 + V_B} \qquad (7)$$

The absorbance $A(1)$ is measured by the photometer in step 118. The measured absorbance is corrected for deviations from Beer's law in step 120 as described below. Then all other corrections (i.e., temperature, etc.) are performed and the pipette volume is calculated in step 122. The pipette volume $P_1$ is the volume to be determined in Equation (7). Solving Equations (6) and (7) for $P_1$ gives $$P_1 = V_B \frac{A(1) - A(o)}{(C_A \epsilon_{A1} l - C_B \epsilon_{B1} l) - (A(1) - A(o))} \qquad (8)$$

All quantities on the right side of Equation (8) are known or have been measured, thereby permitting pipette volume $P_1$ to be calculated.

After the pipette volume $P_1$ has been calculated, the volume measurement process is repeated a predetermined number of times. This is done to verify the repeatability of the pipette operation and also to provide a more accurate determination of pipette volume. Typically, ten volume measurements are taken. After the first volume calculation is completed in step 122, the number of sample readings is checked in step 124. When less than ten sample readings have been completed, the pipette being calibrated is used to transfer a second aliquot $P_2$ of sample solution to the blank reagent cuvette 78 in the photometer. Importantly, the blank reagent cuvette 78 is not emptied or moved from the photometer between volume measurements, thereby insuring that the optical pathlength does not change due to rotation or other movement of the cuvette. The cuvette now contains a volume $P_1 + P_2$ of sample solution. The volume $P_2$ of the second sample solution is calculated in accordance with $$P_2 = V_B \frac{A(2) - A(o)}{(C_A \epsilon_{A1} l - C_B \epsilon_{B1} l) - (A(2) - A(o))} - P_1 \qquad (9)$$

where $A(2)$ is the measured absorbance of the vial after the volume $P_1 + P_2$ of sample solution is added. Since $P_1$ is already known, $P_2$ can be calculated. The process is repeated until the desired number of pipette volumes have been measured. The limit as to how many pipette volumes can be added to the reference solution is either a) the absorbance of the cuvette contents should not exceed $A = 1.7$ or there will be excessive photometer nonlinearity, or b) the contents of the cuvette should not exceed 8.5 milliliters or the mixing action will not be sufficient to insure homogeneity.

After all volume measurements have been taken, statistics are calculated in step 126. The statistics can include average, standard deviation and coefficient of variation. Then the results, including pipette serial number, nominal volume, individual volume readings and statistics, are printed in step 128. The user then removes the cuvette from the photometer, thereby making the photometer ready to begin another volume calibration sequence.

The classic form of Beer's law is given by Equation (1) above. This is accurate for many absorbing species over wide ranges of concentration. However, it is generally accepted to be only a good approximation and not exact. In the reagent system described above which utilizes copper sulfate in the reference solution and Acid Red 1 in the sample solution, there is a slight deviation from Beer's law which can be measured and corrected. When no correction is applied to measured absorbance readings, the calculated pipette volumes show a noticeable decrease toward the end of a run. For example, in the volume calibration of a 100 microliter pipette, the calculated pipette volume for the first sample was 104.36 microliters and the measured absorbance was 0.2254, whereas the calculated pipette volume for the tenth sample was 101.06 microliters and the measured absorbance was 1.700. An analysis of the data indicates that the measured values of absorbance fall off from predicted values at absorbances higher than about one. There are two possible explanations for this trend in the data. One is a deviation from Beer's law. A second explanation is that the instrument is not linear. A prime reason for lack of instrumental linearity would be stray light. A number of tests indicated that the observed effect represents a deviation from Beer's law rather than instrument nonlinearity. Thus, in order to obtain accurate pipette calibration data at absorbances greater than one, a Beer's law correction is introduced.

The form of the correction was determined empirically in order to produce optimum linearity of the results when averaged over many trials. Each time an absorbance $A$ is measured, a corrected absorbance $A_c$ is calculated using $$A_c = K_2 A^2 + K_1 A + K_0 \qquad (10)$$

where the values $K_0$, $K_1$ and $K_2$ are determined by best fit to the data for each range. The values of $K_0$, $K_1$ and $K_2$ are given in Table I below. The corrected absorbance $A_c$ is used in all pipette volume calculations.

TABLE I

|  | $K_0$ | $K_1$ | $K_2$ |
|---|---|---|---|
| Range 1 | −.000785 | +.9788 | +.008795 |

TABLE I-continued

| | $K_0$ | $K_1$ | $K_2$ |
|---|---|---|---|
| (5-20 μl) | | | |
| Range 2 | −.000447 | +.9870 | +.010255 |
| (21-100 μl) | | | |
| Range 3 | −.00126 | +.9854 | +.009273 |
| (101-500 μl) | | | |

The dyes A and B used in the pipette calibration system have a dependence of absorbance on temperature. Temperature dependence was measured for both dyes using a Varian Cary Model 219 Spectrophotometer equipped with a temperature controlled cuvette holder. The absorbance of both dyes was measured in the range of 15° C. to 30° C. The temperature dependence of the absorptivity was found to be linear and of the form $$\epsilon(T) = \epsilon_{15}[1 + K(T-15)] \quad (11)$$

where $\epsilon(T)$ represents the value of the absorptivity at temperature T, $\epsilon_{15}$ represents the value of the absorptivity at 15° C. and K is a constant. The values determined for K were $K_A = +0.01\%/°$ C. and $K_B = +0.14\%/°$ C. The temperature of the dyes as they are used during a pipette calibration is established by requiring that they be stored at the same ambient temperature as the photometer. The photometer accurately measures ambient room temperature at the beginning of a volume calibration in step 104 and thus also measures the temperature of the dyes.

All raw absorbance data as measured at ambient temperature T is corrected to 25° C. using the relationship $$A_{corrected} = A_{measured}\left(\frac{1 + K(25 - 15)}{1 + K(T - 15)}\right) \quad (12)$$

The concentrations of the dyes are adjusted so that correct pipette calibration results (without temperature correction factors being applied) are obtained at an ambient temperature of 25° C. The vials are filled with 3.5378 grams of dye B solution, which occupies a volume of 3500 microliters at 25° C.

The volume of dye B at volume calibration time is dependent on its temperature according to $$V_B(T) \times V_B(25°)[1 + K_V(T-25)] \quad (13)$$

where $V_B(25°) = 3500$ microliters and $K_V = 2.32 \times 10^{-4}$ per ° C. Thus, $V_B(T)$ can be calculated and used in the calculation of pipette volume. The value of $K_V$ is taken to be equal to the volume expansion coefficient for water as obtained from the *Handbook of Physics and Chemistry*.

In order to correct the volume calibration system for temperature effects, two corrections must thus be made: a) both dyes must be corrected for the dependence of their absorptivities on temperature, and b) the volume of dye B must be corrected for its dependence on temperature. Using these factors, the volume calibration system has been found experimentally to be corrected within 0.5% overall accuracy for the temperature range of 18° C. to 28° C.

Figure 7:
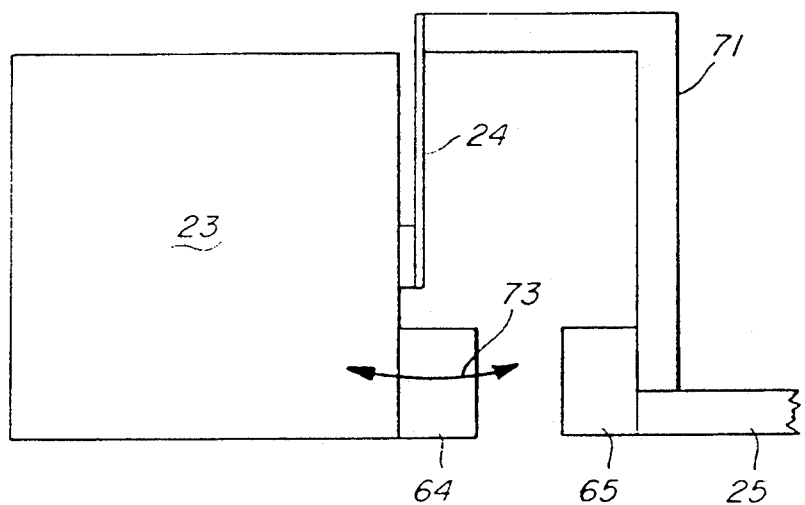
FIG. 7 is a block diagram of a resonant frequency mixing apparatus in the spectrophometer as used in this invention.

FIG. 7 is a block diagram showing a preferred resonant frequency mixing apparatus, such as that described in the aforementioned U.S. Pat. No. 5,092,677, which is incorporated herein by reference. In order to provide for resonant frequency mixing of the contents of the cuvette 27 while disposed in the photometer, the entire optical assembly 23 (shown in FIG. 3) is mounted on a leaf spring 24 and is fitted with a permanent magnet 64 which reacts to an energized electromagnet 65 mounted via support arm 71 on the instrument baseplate 25. Electromagnetic coupling between the electromagnet and the permanent magnet causes an oscillatory motion of the optical assembly in the direction of arrow 73. The electromagnet is activated to drive the optical assembly 23 at its resonant frequency for optimum mixing of the contents of the cuvette.

As described above, dye B comprises copper sulfate having an absorbance peak at 730 rim and dye A comprises Acid Red 1 having an absorbance peak at 520 nm. It will be understood that other dye combinations can be utilized within the scope of the present invention. In general, the requirements on the selection of dye A and dye B include safety for the user, environmental safety, stability, lack of reaction between dye A and dye B, peak absorbances in the visible wavelength range and relatively small overlap of the absorbance spectra. The measurement wavelengths are typically selected to correspond with the absorbance peaks of dye A and dye B. Furthermore, the photometer shown in FIGS. 1, 3 and 4 and described above is not necessarily utilized. Any instrument capable of accurate absorbance measurements can be utilized within the scope of the invention. The microprocessor used for calculating optical pathlengths and volume can be separate from the photometer if desired.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for determining the volume of a vessel using a photometer, comprising the steps of:
    a) positioning a container in a photometer, said container holding a reference solution having maximum absorbance at a first wavelength;
    b) measuring the absorbance of said container at said first wavelength and at a second wavelength;
    c) calculating the optical pathlength of said container at said second wavelength from the measured absorbances at said first and second wavelengths;
    d) introducing an aliquot of a sample solution into said container from a vessel to be calibrated, said sample solution having maximum absorbance at said second wavelength, and mixing said sample solution with said reference solution to form a mixture;
    e) measuring the absorbance of said mixture in said container at said second wavelength; and
    f) calculating the volume of the aliquot from the absorbance of said mixture and the optical pathlength of said container, the volume of said aliquot representing the volume of the vessel.

2. A method as defined in claim 1 further including repeating steps d) through f) to provide multiple measurements of the volume of the vessel without emptying said container or moving said container from its position in said photometer.

3. A method as defined in claim 1 wherein the step of positioning a container holding a reference solution includes using a reference solution comprising copper sulfate dissolved in a buffer, said reference solution having maximum absorbance at about 730 nm.

4. A method as defined in claim 3 wherein the step of introducing an aliquot of sample solution includes using a sample solution comprising Acid Red 1 dissolved in a buffer, said sample solution having maximum absorbance at about 520 nm.

5. A method as defined in claim 1 wherein the step of calculating the optical pathlength includes correcting the optical pathlength for zero offset representative of a difference between the absorbance of said container at said first wavelength and the absorbance of said container at said second wavelength.

6. A method as defined in claim 1 wherein the step of calculating the optical pathlength includes correcting the optical pathlength for a difference between the pathlength of said container at said first wavelength and the pathlength of said container at said second wavelength.

7. A method as defined in claim 1 wherein the step of calculating the volume includes calculating the volume using Beer's law and correcting the calculated volume for deviations from Beer's law.

8. A method as defined in claim 1 further including the step of measuring the ambient temperature and wherein the step of calculating the volume includes correcting the measured absorbance of said mixture for a difference between the absorbance of said mixture at the measured ambient temperature and the absorbance of said mixture at a reference temperature.

9. A method as defined in claim 1 further including the step of measuring the ambient temperature and wherein the step of calculating the volume includes correcting the calculated volume for a difference between the volume at the measured ambient temperature and the volume at a reference temperature.

10. A method as defined in claim 1 wherein said vessel comprises a pipette.

11. A system for use with a photometer in determining the volume of a vessel, comprising:
a first container holding a predetermined volume of a reference solution containing a predetermined concentration of a first light absorping material having maximum absorbence at a first wavelength for positioning in the photometer for determination of the optical pathlength thereof; and
a second container holding a sample solution containing a predetermined concentration of a second light absorping material having maximum absorbence at a second wavelength for transfer with a vessel to be calibrated of an aliquot of sample solution from the second container to the first container for measurement of the absorbence of the mixture of reference and sample solutions at the second wavelength and for determination of the volume of the aliquot from the optical pathlength of the first container and the absorbence of the mixture, the volume of the aliquot representing the volume of the vessel.

12. A system as defined in claim 11, wherein the first container has the capacity to hold multiple transfers of aliquots.

13. A system as defined in claim 11 wherein the second container holds sufficient sample solution for multiple transfers of aliquots to the first container using pipette.

14. A system as defined in claim 11 wherein said reference solution comprises copper sulfate dissolved in a buffer.

15. A system as defined in claim 11 wherein said sample solution comprises Acid Red 1 dissolved in a buffer.

16. A system as defined in claim 11 wherein said vessel comprises a pipette.

17. A system for determining the volume of a vessel, comprising:
a photometer;
a container holding a predetermined volume of a reference solution having maximum absorbance at the first wavelength positioned in said photometer;
said photometer including means for measuring the absorbance of said container holding a reference solution at said first wavelength and at a second wavelength;
means for calculating the optical pathlength of said container at said second wavelength from the measured absorbances at said first and second wavelengths;
said photometer including means for mixing said reference solution with an aliquot of sample solution transferred to said container with a vessel to be calibrated to form a mixture, and means for measuring the absorbance of said mixture at said second wavelength; and
means for calculating the volume of the aliquot from the measured absorbance of said mixture and the optical pathlength of said container, the volume of said aliquot representing the volume of said vessel.

18. A system as defined in claim 17, wherein the container has the capacity to hold multiple transfers of aliquots.

19. A system as defined in claim 17, wherein the calculating means can make volume calculations based on multiple transfers of aliquots.

20. A system as defined in claim 17 wherein said means for calculating the optical pathlength includes means for correcting the optical pathlength for zero offset representative of a difference between the absorbance of said container at said first wavelength and the absorbance of said container at said second wavelength.

21. A system as defined in claim 17 wherein said means for calculating the optical pathlength includes means for correcting the optical pathlength for a difference between the pathlength of said container at said first wavelength and the pathlength of said container at said second wavelength.

22. A system as defined in claim 17 wherein said means for calculating the volume includes means for calculating the volume using Beer's law and means for correcting the calculated volume for deviations from Beer's law.

23. A system as defined in claim 17 further including means for measuring the ambient temperature and wherein said means for calculating the volume includes means for correcting the measured absorbance of said mixture for a difference between the absorbance of said mixture at the measured ambient temperature and the absorbance of said mixture at a reference temperature.

24. A system as defined in claim 17 further including means for measuring the ambient temperature and wherein said means for calculating the volume includes means for correcting the calculated volume for a difference between the volume at the measured ambient temperature and the volume at a reference temperature.

25. A system as defined in claim 17 wherein said reference solution comprises copper sulfate dissolved in a buffer, said reference solution having maximum absorbance at about 730 min.

26. A system as defined in claim 25 wherein the sample solution comprises Acid Red 1 dissolved in a buffer, said sample solution having maximum absorbance at about 520 nm.

27. A system as defined in claim 1 wherein said vessel comprises a pipette.

28. A method for measuring the optical pathlength of a container to be used for absorbence measurements at a predetermined wavelength, comprising the steps of:
positioning a container in a photometer, said container holding a reference solution having maximum absorbance at a first wavelength that is different from the predetermined wavelength;
measuring the absorbence of said container at said first wavelength and at said predetermined wavelength;
calculating the optical pathlength of said container at said predetermined wavelength from the measured absorbences at said first wavelength and said predetermined wavelength;
adding a sample solution to the container and making at least one absorbence measurement of the sample solution in the container at a predetermined wavelength; and
removing the container from the photometer and subsequently positioning another container in the photometer and repeating the above-defined steps.

29. A method as defined in claim 28 wherein the step of calculating the optical pathlength includes correcting the optical pathlength for zero offset representative of a difference between the absorbance of said container at said first wavelength and the absorbance of said container at said predetermined wavelength.

30. A method as defined in claim 28 wherein the step of calculating the optical pathlength includes correcting the optical pathlength for a difference between the pathlength of said container at said first wavelength and the pathlength of said container at said predetermined wavelength.

* * * * *

UNITED STATES PATENT AND TRADEMARK OFFICE
CERTIFICATE OF CORRECTION

PATENT NO. : 5,298,978  
DATED : March 29, 1994  
INVENTOR(S) : Curtis, et al

Page 1 of 2

It is certified that error appears in the above-indentified patent and that said Letters Patent is hereby corrected as shown below:

Col. 6, line 13 - delete "rim" and substitute -- nm --.
Col. 6, line 66 - " " " "
Col. 7, line 23 - " " " "
Col. 8, line 25 - " " " "
Col. 8, line 33 - " " " "
Col. 9, line 6 - " " " "
Col. 9, line 28 - " " " "
Col. 12, line 15 - " " " "
Col. 7, line 48 - after "730" insert -- nm. --
Col. 13, line 5 - delete "run" and substitute -- nm --
Col. 15, line 6 - delete "min" and substitute -- nm --.
Col. 7, line 31 - delete "l" and substitute -- $\ell$ --.
Col. 7, line 37 - delete "l" and substitute -- $\ell$ --.

Col. 8, equation (5) should read:

$$P_{Aeff} = \frac{f_{520}}{f_{730}} \cdot \frac{A\ round\ (520)}{A\ square\ (520)} \cdot \frac{A\ square\ (730)}{A\ round\ (730)} \quad (5)$$

UNITED STATES PATENT AND TRADEMARK OFFICE
CERTIFICATE OF CORRECTION

PATENT NO. : 5,298,978
DATED : March 29, 1994
INVENTOR(S) : Curtis, et al

It is certified that error appears in the above-indentified patent and that said Letters Patent is hereby corrected as shown below:

Col. 9, equation (6) should read:

$$A_0 = A(o) - \epsilon_{Bl} C_B \ell \qquad (6)$$

Col. 11, equation (13) should read:

$$V_B(T) = V_B(25°)\left[1 + K_V(T - 25)\right] \qquad (13)$$

Signed and Sealed this

Sixth Day of December, 1994

Attest:

BRUCE LEHMAN

*Attesting Officer*     *Commissioner of Patents and Trademarks*